US008884074B2

(12) United States Patent
Ahlers et al.

(10) Patent No.: US 8,884,074 B2
(45) Date of Patent: Nov. 11, 2014

(54) METHOD AND DEVICE FOR PRODUCING DIMETHYL ETHER FROM METHANOL

(75) Inventors: Bernd Ahlers, Dietzenbach (DE); Gerhard Birke, Frankfurt am Main (DE); Harald Koempel, Neu-Isenburg (DE); Hermann Bach, Heiligenroth (DE); Martin Rothaemel, Frankfurt am Main (DE); Waldemar Liebner, Oberursel (DE); Walter Boll, Frankfurt am Main (DE); Veronika Gronemann, Karben (DE)

(73) Assignee: Air Liquide Global E&C Solutions Germany GmbH, Frankfurt am Main (DE)

( * ) Notice: Subject to any disclaimer, the term of this patent is extended or adjusted under 35 U.S.C. 154(b) by 715 days.

(21) Appl. No.: 13/130,611

(22) PCT Filed: Nov. 19, 2009

(86) PCT No.: PCT/EP2009/008237

§ 371 (c)(1), (2), (4) Date: Aug. 16, 2011

(87) PCT Pub. No.: WO2010/060566

PCT Pub. Date: Jun. 3, 2010

(65) Prior Publication Data

US 2011/0295043 A1 Dec. 1, 2011

(30) Foreign Application Priority Data

Nov. 25, 2008 (DE) ......................... 10 2008 058 931

(51) Int. Cl.

| | |
|---|---|
| ***C07C 41/09*** | (2006.01) |
| ***B01J 19/00*** | (2006.01) |
| ***B01D 3/14*** | (2006.01) |

(52) U.S. Cl.

CPC ................ *C07C 41/09* (2013.01); *B01D 3/143* (2013.01)

USPC .......................................... 568/698; 422/187

(58) Field of Classification Search

USPC .................................. 568/698, 699; 422/187

See application file for complete search history.

(56) References Cited

U.S. PATENT DOCUMENTS

| | | | |
|---|---|---|---|
| 5,750,799 | A | 5/1998 | Van Dijk |
| 6,740,783 | B1 | 5/2004 | Jun et al. |
| 2010/0240932 | A1 | 9/2010 | Park et al. |

FOREIGN PATENT DOCUMENTS

| | | | |
|---|---|---|---|
| CA | 1322767 | C | 10/1993 |
| CA | 100366597 | C | 2/2008 |
| CN | 1830934 | A | 9/2006 |
| EP | 0455004 | A1 | 11/1991 |
| EP | 1396483 | A1 | 3/2004 |
| JP | 2004161672 | A | 6/2004 |
| JP | 2004161673 | A | 6/2004 |
| WO | WO 2008026887 | A1 | 3/2008 |

*Primary Examiner* — Rosalynd Keys

(74) *Attorney, Agent, or Firm* — Leydig, Voit & Mayer, Ltd.

(57) ABSTRACT

A process produces dimethyl ether (DME) from methanol (MeOH). The process includes charging a feed mixture consisting of raw MeOH and a process-internally obtained return flow substantially consisting of unconverted MeOH and reaction water to an MeOH column. The feed mixture is evaporated in the MeOH column to form a first distillate substantially consisting of vaporous MeOH. The first distillate is supplied to a reactor and the MeOH is converted to DME by splitting off water in the reactor so as to form a reaction mixture. The reaction mixture is withdrawn from the reactor, charged to a mixture column and separated into a bottom product substantially consisting of water and a second distillate substantially consisting of DME and MeOH. The second distillate is separated in a DME column into a third distillate substantially consisting of DME, a bottom product consisting essentially of water-poor MeOH, and uncondensable gases discharged overhead. The bottom product is either supplied to a top of the MeOH column or mixed with another bottom product withdrawn from a forerun column.

22 Claims, 2 Drawing Sheets low boiler
DME
water
1
2
3
4
5
6
7
8
10
11
12
13
14
15
16
17
18
19
20
21
22
23
24
25
26
27
28
29

METHOD AND DEVICE FOR PRODUCING DIMETHYL ETHER FROM METHANOL

CROSS REFERENCE TO RELATED APPLICATIONS

This application is a U.S. National Phase application under 35 U.S.C. §371 of International Application No. PCT/EP2009/008237, filed on Nov. 19, 2009, and claims benefit to German Patent Application No. DE 10 2008 058 931.4, filed on Nov. 25, 2008. The International Application was published in German on Jun. 3, 2010 as WO 2010/060566 A1 under PCT Article 21 (2).

FIELD

This invention relates to a process and an apparatus for producing dimethyl ether (DME) from methanol (MeOH) by converting raw MeOH obtained through MeOH synthesis to DME by splitting off water in a reactor.

BACKGROUND

Nowadays, MeOH exclusively is produced from the synthesis gases $CO_2/H_2$ or $CO/H_2$, which in turn originate from the reforming of natural gas, residue oils of crude oil processing or from the pressure gasification of coal. The raw MeOH produced can directly be processed to DME or be processed by distillation to obtain pure MeOH and subsequently be catalytically converted to DME and water. In both cases, the DME product obtained is separated from unconverted MeOH and water by distillation. In general, the raw MeOH is subjected to a two- or three-stage distillation, in which first the low boilers and the dissolved gases, in particular $CO_2$, are removed and then MeOH and water are separated, and in an adiabatic fixed-bed reactor the purified MeOH is converted to DME up to the reaction equilibrium. Since the reactor product comprises a mixture of DME, water, unconverted MeOH and minor amounts of uncondensable light gases, the reactor product is treated in a two-stage distillation, wherein in the head of the first distillation stage DME is separated from unconverted MeOH and reaction water and in the head of the second distillation stage the MeOH contained in the bottom product of the first stage is separated from the reaction water and the MeOH obtained flows back into the reactor. The uncondensable light gases discharged with the DME at the top of the first distillation stage are saturated with DME which in a gas washing stage is separated from the uncondensable gases by using MeOH as washing agent, before the same leave the system as low boilers at the top of the gas washing stage. Accordingly, both in the distillation of DME and in the distillation of MeOH mixtures chiefly comprising MeOH, water and DME are separated. Since the product specifications for DME on the one hand and MeOH on the other hand must satisfy various requirements, the distillations of DME and MeOH are carried out separately. The above-described measures are applied in particular for the production of high-purity DME, which is widely used as propellant gas, e.g. in hair spray and paint spray. Technical DME is an alternative to liquefied gases with excellent burning properties. Due to a cetane number of 55 to 60, DME can be used in diesel engines as a substitute for diesel fuel.

Since according to the Biofuels Directive 2003/30/EG of the European Parliament and the "Council for Promoting the Use of Biofuels or other Renewable Fuels in the Transport Sector" DME is regarded as biofuel, the same may contain impurities which are not allowed for high-purity DME.

Therefore, the distillation of the MeOH can be omitted and the raw MeOH can directly be charged to the DME reactor. In the process described in U.S. Pat. No. 5,750,799 A, for example, untreated raw MeOH is directly introduced into a DME reactor, so that the return flow containing the MeOH is loaded with considerable amounts of water. This circulating water must be condensed in addition to the unconverted MeOH and must subsequently be evaporated before the DME reactor, whereby the energy efficiency of the process is impaired considerably. In addition, the circulating stream is increased due to the reduced MeOH conversion in the DME reactor and accordingly the apparatuses and technical components of the plant for producing DME must be designed larger. Raw MeOH contains carbonic acid $H_2CO_3$ and small amounts of organic acids which must be neutralized, in order to avoid corrosion phenomena on apparatuses and technical components made of steel, which are used for producing DME. Usually soda is used for neutralizing the raw MeOH.

U.S. Pat. No. 6,740,783 B1 describes a process for producing DME from raw MeOH by using a DME reactor with a fixed bed of zeolite catalyst which initially is deactivated by doping with metals, in order to increase the DME selectivity of the catalyst. On the long run, however, a constant supply of metals leads to a continuous deactivation and hence to a reduction of the useful life of the catalyst. The subject-matter of EP 1396483 B1 is a process for producing DME, in which raw MeOH is dehydrated in the vapor phase in the presence of an activated $Al_2O_3$ catalyst doped with Na. A limited doping with Na is important, so as not to impair the conversion of the catalyst. This means that the raw MeOH must be largely free from metal and $NH_4$ ions. In the provided raw MeOH and its evaporation the entrainment of neutralizing agent must therefore be carefully avoided.

In the documents CN 100366597 C, CN 1830934 A and JP 2004161673 A apparatuses are described, in which raw MeOH and reflux MeOH are supplied to a common separating means. The reflux MeOH contains the entire reaction water originating from the DME reactor, so that the reflux MeOH cannot be charged to the top of the distillation column. Therefore, the use of an overhead condenser is provided, in order to lower the water content of the raw MeOH supplied to the DME reactor. This requires a considerable condenser capacity which involves a correspondingly greater performance of the reboiler, whereby the energy efficiency and the economy are reduced. JP 2004161672 A deals with an evaporator for raw MeOH, which allows a partial evaporation of the raw MeOH, wherein the non-evaporated mixture of MeOH and water together with the unconverted MeOH and the reaction water from the DME reactor is separated into process water and reflux MeOH in a separate distillation column operating at low pressure. The subcooled water-poor liquid reflux MeOH is contacted with the evaporated raw MeOH, so that the water concentration in the raw MeOH supplied to the DME reactor is lowered. Hence, it is provided to also pass non-evaporated MeOH to the reflux MeOH column along with the non-evaporated water of the raw MeOH. This measure requires the evaporation and condensation of the MeOH in the reflux MeOH column and after the return of the largely water-free MeOH to the raw MeOH evaporator the renewed evaporation of the same MeOH. Thus, a MeOH circuit without contact with the DME reactor is obtained, which consumes unnecessary energy and reduces the efficiency of the circuit.

EP 455004 A1 or U.S. Pat. No. 5,750,799 A describe washing out in a column the DME discharged with the uncondensable gases at the head of the DME column and recirculating the same to the MeOH column. This measure leads to a DME content in the raw MeOH charged to the DME reactor, by which the conversion of MeOH to DME is reduced. This is relevant in particular when raw MeOH is used and the light gases contained in the raw MeOH are not separated before the DME reactor, but only in the DME column. Proportional to the amount of the non-condensed light gases, the amount of the DME discharged with the gases and hence the amount of DME in the inflow to the DME reactor increases.

When the raw MeOH contains only little dissolved gases, the arrangement of a scrubber can be omitted. Instead, the DME discharged with the uncondensable gases can largely be recovered in an end cooler operated with cold water or a refrigerant.

SUMMARY

In an embodiment, the present invention provides a process for producing dimethyl ether (DME) from methanol (MeOH). The process includes charging a feed mixture comprising raw MeOH and a process-internally obtained return flow substantially comprising unconverted MeOH and reaction water to an MeOH column. The feed mixture is evaporated in the MeOH column to form a first distillate substantially comprising vaporous MeOH. The first distillate is supplied to a reactor and the MeOH is converted to DME by splitting off water in the reactor so as to form a reaction mixture. The reaction mixture is withdrawn from the reactor, charged to a mixture column and separated into a bottom product substantially comprising water and a second distillate substantially comprising DME and MeOH. The second distillate is separated in a DME column into a third distillate substantially comprising DME, a bottom product essentially comprising water-poor MeOH, and uncondensable gases discharged overhead. The bottom product is either supplied to a top of the MeOH column or mixed with another bottom product withdrawn from a forerun column.

BRIEF DESCRIPTION OF THE DRAWINGS

Exemplary embodiments of the present invention are described in more detail below with respect to the drawings, in which.

Figure 1:
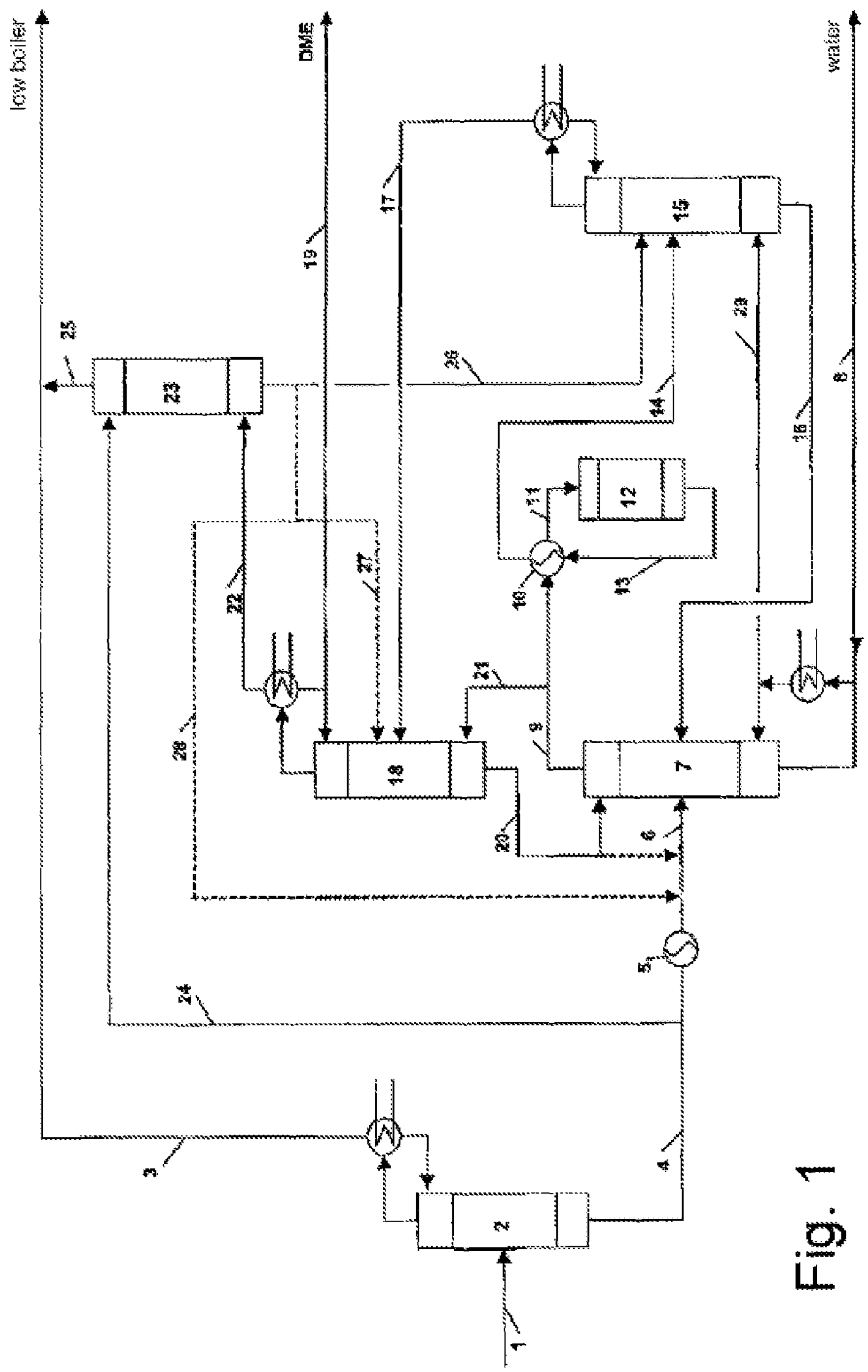
FIG. 1 shows a process flow diagram according to an embodiment of the invention.

The features described in more detail below and shown in the drawings can be combined in any manner.

DETAILED DESCRIPTION

An embodiment of the present invention relates to a process and an apparatus for producing dimethyl ether (DME) from methanol (MeOH) by converting, preferably by acid-catalytic condensation, raw MeOH obtained through MeOH synthesis to DME by splitting off water in a reactor, in which the feed mixture comprising raw MeOH and a process-internally obtained return flow substantially formed from unconverted MeOH and reaction water are charged to a column, subsequently referred to as MeOH column, and evaporated, and the distillate substantially comprising vaporous MeOH is supplied to the reactor.

In an embodiment, the present invention provides a process for producing DME from MeOH in which a rather low consumption of operating resources is achieved, the installed heat transfer capacity is improved and the useful life of the catalyst is not impaired.

An embodiment of the present invention provides that in a column, subsequently referred to as mixture column, the reaction mixture withdrawn from the reactor is separated into a bottom product chiefly comprising water and into a distillate chiefly formed from DME and MeOH, in a column, subsequently referred to as DME column, the distillate is separated into a distillate substantially containing DME and uncondensable gases to be released overhead and into a bottom product formed from water-poor MeOH, which is supplied to the top of the MeOH column.

The term "distillate" defines the product withdrawn in a distillation or rectification column as side product or as top product.

In an embodiment, the bottom product of the DME column, which is formed from water-poor MeOH, is supplied to the top of the MeOH column or mixed with the bottom product withdrawn from the forerun column.

It is possible to cool or partly condense the reaction mixture withdrawn from the reactor in a process-internal heat exchanger, before the reaction mixture is charged to the mixture column.

The amount of water of the distillate of the mixture column, which is introduced into the DME column and chiefly comprises DME and MeOH, can be adjustable via the reflux ratio of the amount of liquid produced at the top of the column by condensation of a part of the top product and charged again at the top of the column and the amount of top product discharged to the DME column. By means of this measure, the quality of the water-poor liquid reflux MeOH withdrawn from the bottom of the DME column can be optimized.

In an embodiment, a part of the vapor produced by evaporating the return flow of the bottom product of the MeOH column substantially comprising water can be introduced into the bottom of the mixture column and in this way the DME content in the bottom is decreased.

In an embodiment, the distillate of the DME column substantially comprising DME is condensed and one part of the condensate is charged as return flow to the top of the DME column and the other part of the DME condensate is discharged. Due to the fact that at the same time the bottom product of the DME column comprising water-poor liquid MeOH is charged to the top of the MeOH column, the condensation in the MeOH column can be omitted.

It is also possible that the DME condensed in the DME column is discharged from the fortification section of the DME column as side product.

In an embodiment, the DME discharged with the uncondensable gases is washed out in a washing column, preferably with MeOH, and passed into the mixture column.

Further, the gases and low-boiling components dissolved in the inflowing raw MeOH can be separated from the inflowing raw MeOH before evaporation of the MeOH in the MeOH column and the distillate is discharged, whereby the quality of the DME produced is improved and the amount of DME entrained from the DME column with the uncondensable gases is reduced.

The bottom product withdrawn from the forerun column can be preheated and/or partly evaporated before flowing into the MeOH column.

In an embodiment, the DME discharged with the uncondensable gases at the top of the DME column can be washed out in a washing column, preferably with MeOH, and the bottom product produced is passed into the DME column and/or added to the raw MeOH prior to entry into the MeOH column.

In accordance with another embodiment, raw MeOH branched off from the inflow of the raw MeOH can be charged to the top of the washing column as washing agent.

When the raw methanol contains only small amounts of dissolved gases, the arrangement of a washing column can be omitted and instead an end cooler operated with cold water or refrigerant, for example DME, can be used, with which the DME discharged with the uncondensable gases can be recovered.

It is expedient to combine the distillate of the forerun column, which contains dissolved gases and low-boiling components, with the distillate of the washing column, which contains uncondensable gases, and to discharge the mixture for further processing.

In an embodiment, the bottom product of the MeOH column, which chiefly comprises water, is discharged from the process or supplied to the lower part of the mixture column and then discharged via the bottom of the mixture column.

It is also possible that the bottom product of the mixture column, which chiefly comprises water, is passed into the MeOH column and the water is discharged from the process via the bottom of the MeOH column.

It is advantageous that before introduction into the reactor the distillate of the MeOH column, which contains MeOH, is superheated to a reaction temperature of 250 to 330° C. by indirect heat transfer from the reaction heat contained in the reaction mixture discharged from the reactor.

A part of the gaseous distillate of the MeOH column is passed into the bottom of the DME column.

In an embodiment of an apparatus in accordance with the invention for carrying out the process the DME column is arranged on the MeOH column. The two columns are coupled via the distillate of the MeOH column and the bottom product of the DME column, so that the MeOH column can be operated without reflux cooler and the DME column can be operated without evaporator.

In another embodiment, the vaporous distillate of the mixture column, which chiefly comprises DME and MeOH, is fed into the bottom of a rectification column, subsequently referred to as DME product column, the bottom product of this column, which contains liquid MeOH, is charged to the top of a rectification column, subsequently referred to as MeOH reflux column, wherein the distillate thereof is passed into the bottom of the DME product column and the bottom product thereof is supplied to the top of the MeOH column.

In this modification, the DME product column formed as fortification section is arranged on the mixture column and the MeOH reflux column formed as stripping section is arranged on the MeOH column. By means of this measure, the fortification section and the stripping section of the DME column virtually are separated and the smaller stripping section of the DME column can be put onto the methanol column and the larger fortification section of the DME column can be put onto the mixture column. The diameters of the mixing column and of the fortification section of the DME column are almost the same.

According to FIG. 1, a feed stream comprising raw MeOH with an MeOH content of 75 wt-% is fed via conduit (1) into the forerun column (2) in which at a mean temperature of 80° C. and a mean pressure of 3 bar[a] the gases dissolved in the raw MeOH, such as CO, $CO_2$, $CH_4$, and the low-boiling hydrocarbons are discharged via conduit (3) for further utilization. The MeOH withdrawn with a mean temperature of 100° C. from the bottom of the forerun column (2) via conduit (4) is preheated to a mean temperature of 160° C. in a heat exchanger group (5), partly evaporated thereby and charged via conduit (6) to a MeOH column (7) in which the water is separated from the MeOH at a mean temperature of 180° C. and a mean pressure of 20 bar[a]. From the bottom of the MeOH column (7) the water is discharged from the process via conduit (8), while the gaseous top product of the MeOH column, which is discharged via conduit (7) with a mean temperature of 170° C., is heated to a mean temperature of 300° C. in a heat exchanger group (10) and passed into a reactor (12) via conduit (11). The gas mixture withdrawn at the bottom of the reactor (12) is supplied to the heat exchanger group (10) via conduit (13) and cooled recuperatively, before it is charged to the mixture column (15) via conduit (14). In the mixture column (15) the gas mixture is separated into a water-rich bottom product and a water-poor top product at a mean pressure of 15 bar[a] and a mean temperature of 150° C., wherein the top product contains less than 5 wt-%, preferably less than 2 wt-% of water. The water-rich bottom product is passed to the MeOH column (7) via conduit (16). The water-poor top product is supplied via conduit (17) to the DME column (18) which operates at a mean temperature of 100° C. and a pressure of 13.5 bar[a]. From the top of the DME column (18) or from the side, two to seven trays below the overhead condenser, DME is withdrawn and passed to the plant boundary via conduit (19). The bottom product of the DME column (18), which chiefly comprises MeOH with small amounts of water, is pumped to the top of the MeOH column (7) via conduit (20) and serves as return flow for the fortification section of the MeOH column (7). To keep the concentration of DME in the bottom of the DME column (18) as low as possible, a partial stream of the top product of the MeOH column (7) flowing in conduit (9) can be branched off and be introduced into the bottom of the DME column (18) via conduit (21), so that in this case an evaporator circuit can be omitted.

The gases not condensable in the DME column (18) are withdrawn overhead and passed via conduit (22) into the bottom of the washing stage (23) in which the DME contained in the uncondensable gases is recovered at a mean pressure of 10 bar[a] and a mean temperature of 75° C. along with the MeOH branched off from conduit (4) and charged to the top of the washing stage (23) via conduit (24). Via conduit (25) the gaseous top product of the washing stage (23) is combined with the top product of the forerun column (2) flowing off via conduit (3) and discharged for further utilization. Via conduit (26) the washing agent containing DME is pumped from the bottom of the washing stage (23) into the mixture column (15). Alternatively, the bottom product of the washing stage (23) can either be fed into the DME column (18) via conduit (27) or be fed via conduit (28) into the MeOH stream flowing to the MeOH column (7) in conduit (6). The mixture column (15) can be operated without evaporator circuit.

Figure 2:
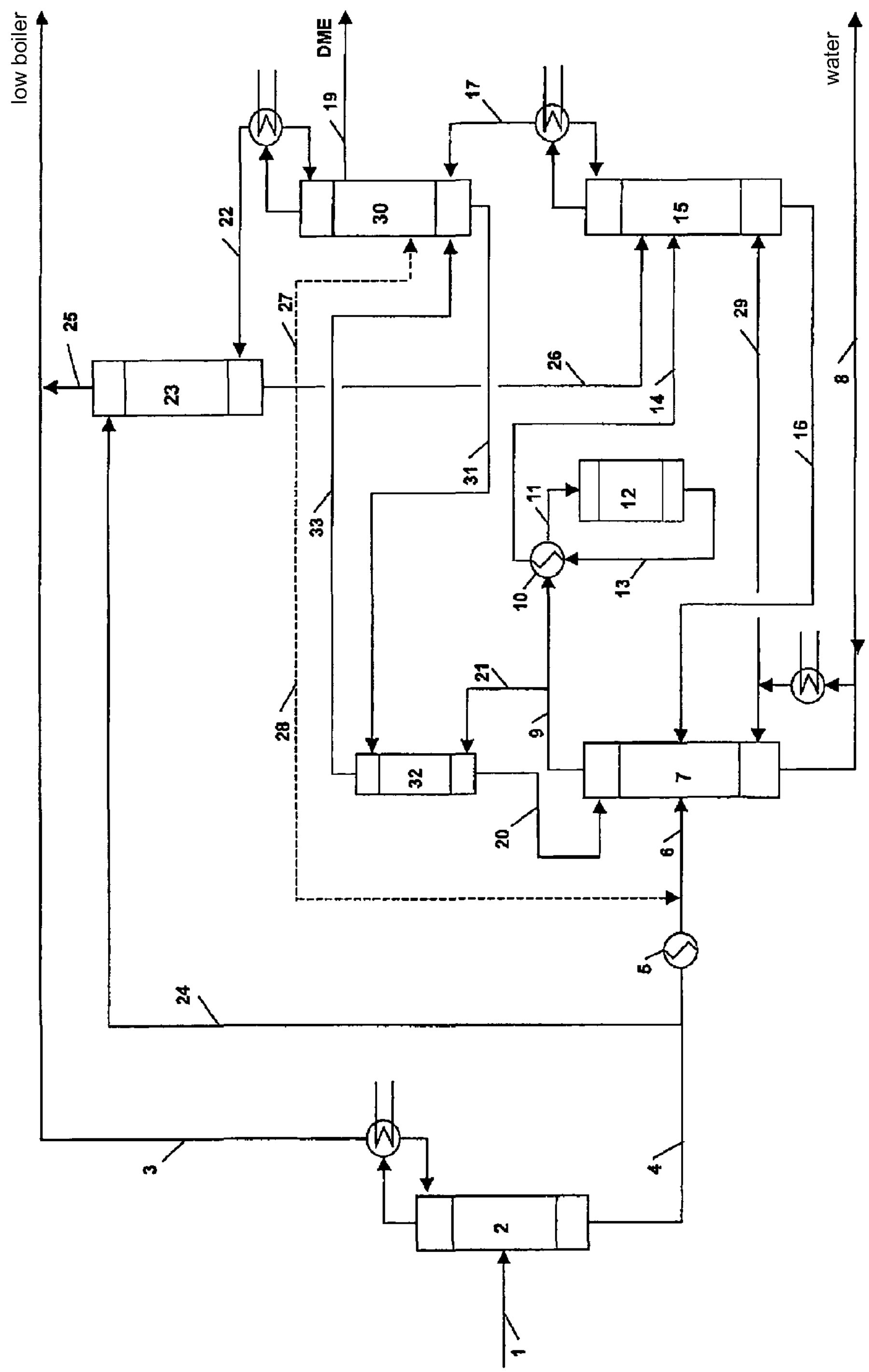
FIG. 2 shows a process flow diagram in accordance with another embodiment of the invention.

In a modification of the process flow diagram according to FIG. 1, which is represented in FIG. 2, the water-poor product discharged from the top of the mixture column (15) via conduit (17) is directly passed into the bottom of a rectification column (30), subsequently referred to as DME product column, which is formed as a fortification column mounted on the mixture column (15). The bottom product of the DME product column (30), which chiefly comprises MeOH with small amounts of water, is supplied via conduit (31) to the top of a column (32), subsequently referred to as MeOH reflux column, which is formed as stripping column and arranged on the MeOH column (7). Via conduit (20) the bottom product of the MeOH reflux column (32) flows to the top of the MeOH column (7), while the top product is passed into the bottom of the DME product column (30) via conduit (33). The partial stream branched off from the top product of the MeOH column (7) flowing in conduit (9) is supplied to the bottom of the MeOH reflux column (32) via conduit (21).

Embodiments of the present invention provide a comparatively improved energy efficiency and economy. A comparison of the process of the invention with a known process belonging to the prior art, as described for example in JP 2004161672 A, shows that under the same marginal conditions for the MeOH content of the raw MeOH, the preheating and partial evaporation of the MeOH prior to entry into the MeOH column, the inlet temperature into the reactor, the purity of the DME produced and the purity of the process water obtained, and with almost the same external energy consumption, the totally installed heat exchanger performance is smaller than in the known process by about 20%.

While the invention has been particularly shown and described with reference to preferred embodiments thereof, it will be understood by those skilled in the art that various changes in form and details may be made therein without departing from the spirit and scope of the invention.

What is claimed is:

1. A process for producing dimethyl ether (DME) from methanol (MeOH), the process comprising:

charging a feed mixture comprising raw MeOH and a process-internally obtained return flow substantially comprising unconverted MeOH and reaction water to an MeOH column;

evaporating, in the MeOH column, the feed mixture so as to form a first distillate substantially comprising vaporous MeOH;

supplying the first distillate to a reactor;

converting the MeOH to DME by splitting off water in the reactor so as to form a reaction mixture;

withdrawing the reaction mixture from the reactor;

charging the reaction mixture to a mixture column;

separating, in the mixture column, the reaction mixture into a mixture column bottom product substantially comprising water and a second distillate substantially comprising DME and MeOH;

separating, in a DME column, the second distillate into a third distillate substantially comprising DME and an uncondensable gas discharged overhead, and a DME column bottom product comprising water-poor MeOH; and at least one of supplying the DME column bottom product to a top of the MeOH column, or mixing the DME column bottom product with a forerun column bottom product.

2. The process recited in claim 1, wherein the converting the MeOH to DME comprises acid-catalyzed condensation.

3. The process recited in claim 1, further comprising:

cooling the reaction mixture withdrawn from the reactor before charging the reaction mixture to the mixture column.

4. The process recited in claim 1, further comprising:

condensing at least a portion of the second distillate and returning the portion to a top of the mixture column; and adjusting an amount of water in the second distillate according to a reflux ratio of a condensed liquid amount returned to the top of the mixture column, and a mixture column top product amount discharged to the DME column.

5. The process recited in claim 1, further comprising:

evaporating at least a portion of a MeOH column bottom product, substantially comprising water, to form a MeOH column bottoms vapor; and passing at least a portion of the MeOH column bottoms vapor into a bottom of the mixture column.

6. The process recited in claim 1, further comprising:

condensing the third distillate so as to form a condensate;

charging a first portion of the condensate to a top of the DME column as return flow; and discharging a second portion of the condensate.

7. The process recited in claim 1, further comprising:

discharging, from an ascending section of the DME column, as a DME column side product, DME condensed in the DME column.

8. The process recited in claim 1, further comprising:

washing at least a portion of the third distillate in a washing column, to obtain washed out DME; and passing at least a portion of the washed out DME into the mixture column.

9. The process recited in claim 1, further comprising:

washing at least a portion of the third distillate in a washing column, to obtain washed out DME and MeOH; and passing at least a portion of the washed out DME and MeOH into the mixture column.

10. The process recited in claim 1, further comprising, before the evaporating in the MeOH column:

separating the raw MeOH in the forerun column, so as to form a fourth distillate comprising a low-boiling component of the raw MeOH; and discharging the fourth distillate from the process.

11. The process recited in claim 1, further comprising, before charging the raw MeOH into the MeOH column:

preheating, evaporating, or preheating and evaporating the raw MeOH.

12. The process recited in claim 1, further comprising:

washing at least a portion of the third distillate in a washing column, to obtain a washed out DME; and at least one of passing a washing column bottom product to the DME column, and adding the washing column bottom product to the raw MeOH before charging the raw MeOH into the MeOH column.

13. The process recited in claim 1, further comprising:

washing at least a portion of the third distillate in a washing column, to obtain a washed out DME and MeOH; and at least one of passing a washing column bottom product to the DME column, and adding the washing column bottom product to the raw MeOH before charging the raw MeOH into the MeOH column.

14. The process recited in claim 1, further comprising:

charging to a top of the washing column a washing agent comprising a portion of the raw MeOH, a portion of the DME column bottom product, or both.

15. The process recited in claim 1, further comprising:

combining a fourth distillate formed in the forerun column, comprising a low-boiling component, with a washing column top product comprising an uncondensable gas.

16. The process recited in claim 1, further comprising:

passing at least a portion of a MeOH column bottom product, substantially comprising water, into a lower part of the mixture column; or discharging at least a portion of the MeOH column bottom product from the process.

17. The process recited in claim 1, further comprising:

passing at least a portion of a mixture column bottom product, substantially comprising water, into the MeOH column; or discharging at least a portion of the mixture column bottom product of the mixture column from the process.

18. The process recited in claim 1, further comprising:
superheating the first distillate to a reaction temperature of 250 to 330° C. by indirect heat transfer from a reaction heat contained in the reaction mixture discharged from the reactor.

19. The process recited in claim 1, further comprising:
passing at least a portion of the first distillate into a bottom of the DME column.

20. A process for producing dimethyl ether (DME) from methanol (MeOH), the process comprising:
charging a feed mixture comprising raw MeOH and a process-internally obtained return flow comprising unconverted MeOH and reaction water to an MeOH column;
evaporating, in the MeOH column, the feed mixture so as to form a first distillate comprising vaporous MeOH;
supplying the first distillate to a reactor;
converting the MeOH to DME by splitting off water in the reactor so as to form a reaction mixture;
withdrawing the reaction mixture from the reactor;
charging the reaction mixture to a mixture column;
separating, in the mixture column, the reaction mixture into a bottom product comprising water and a second distillate comprising DME and MeOH;
feeding the second distillate into a bottom of a DME product column;
charging a DME product column bottom product, comprising liquid MeOH, into a top of an MeOH reflux column so as to form a third distillate;
passing the third distillate into the bottom of the DME product column; and
at least one of charging a MeOH reflux column bottom product to a top of the MeOH column, or mixing the MeOH reflux column bottom product with a forerun column bottom product.

21. A plant for producing dimethyl ether (DME) from methanol (MeOH), the plant comprising:
an MeOH column configured to receive a feed mixture comprising raw MeOH and a process-internally obtained return flow substantially comprising MeOH and reaction water and to evaporate the feed mixture so as to form a first distillate substantially comprising vaporous MeOH;
a reactor configured to receive the first distillate and convert the MeOH to DME by splitting off water so as to form a reaction mixture;
a mixture column configured to receive the reaction mixture and to separate the reaction mixture into a bottom product comprising water and a second distillate comprising DME and MeOH; and
a DME column disposed on the MeOH column and configured to receive the second distillate and to separate the second distillate into a third distillate comprising DME and an uncondensable gas as overhead discharge, and a DME column bottom product comprising water-poor MeOH,
wherein the plant is configured to supply the DME column bottom product to a top of the MeOH column or to mix the DME column bottom product with a forerun column bottom product.

22. A plant for producing dimethyl ether (DME) from methanol (MeOH), the plant comprising:
an MeOH column configured to receive a feed mixture consisting of raw MeOH and a process-internally obtained return flow comprising unconverted MeOH and reaction water and to evaporate the feed mixture so as to form a first distillate comprising vaporous MeOH;
a reactor configured to receive the first distillate and convert the MeOH to DME by splitting off water so as to form a reaction mixture;
a mixture column configured to receive the reaction mixture and to separate the reaction mixture into a bottom product comprising water and a second distillate comprising DME and MeOH; and
a DME product column configured as a fortification column and disposed on the mixture column, the DME product column configured to receive the second distillate; and
an MeOH reflux column configured as a stripping column and disposed on the MeOH column, the MeOH reflux column being configured to receive a DME product column bottom product comprising liquid MeOH, to form a third distillate, and to discharge the third distillate into a bottom of the DME product column,
wherein the plant is configured to charge a MeOH reflux column bottom product to a top of the MeOH column or to mix the MeOH reflux column bottom product with a forerun column bottom product.

* * * * *